(12) United States Patent
Koike

(10) Patent No.: US 11,033,193 B2
(45) Date of Patent: Jun. 15, 2021

(54) LIGHT EMITTING DEVICE, BIOLOGICAL INFORMATION MEASURING APPARATUS, AND METHOD OF MANUFACTURING LIGHT EMITTING DEVICE

(71) Applicant: SEIKO EPSON CORPORATION, Tokyo (JP)

(72) Inventor: Shigemitsu Koike, Suwa (JP)

(73) Assignee: SEIKO EPSON CORPORATION, Tokyo (JP)

( * ) Notice: Subject to any disclaimer, the term of this patent is extended or adjusted under 35 U.S.C. 154(b) by 389 days.

(21) Appl. No.: 15/854,245

(22) Filed: Dec. 26, 2017

(65) Prior Publication Data

US 2018/0192901 A1 Jul. 12, 2018

(30) Foreign Application Priority Data

Jan. 10, 2017 (JP) .............................. JP2017-001672

(51) Int. Cl.
| | |
|---|---|
| H01L 31/173 | (2006.01) |
| H01L 33/60 | (2010.01) |
| A61B 5/024 | (2006.01) |
| H01L 31/02 | (2006.01) |
| H01L 33/62 | (2010.01) |
| H01L 31/167 | (2006.01) |
| H01L 25/16 | (2006.01) |

(52) U.S. Cl.
CPC .... *A61B 5/02427* (2013.01); *H01L 31/02019* (2013.01); *H01L 31/167* (2013.01); *H01L 31/173* (2013.01); *H01L 33/60* (2013.01); *H01L 33/62* (2013.01); *A61B 2562/0238* (2013.01); *H01L 25/167* (2013.01); *H01L 2933/0058* (2013.01); *H01L 2933/0066* (2013.01)

(58) Field of Classification Search
CPC . A61B 5/681; A61B 5/02427; A61B 5/02438; A61B 5/6824; H01L 2924/1204; H01L 2924/12041
See application file for complete search history.

(56) References Cited

U.S. PATENT DOCUMENTS

| | | | |
|---|---|---|---|
| 6,184,544 B1 * | 2/2001 | Toda | ..................... H01L 33/486 257/100 |
| 2006/0118800 A1 | 6/2006 | Kim | |
| 2010/0301317 A1 * | 12/2010 | Nowatari | ............ H01L 51/5278 257/40 |

(Continued)

FOREIGN PATENT DOCUMENTS

| | | |
|---|---|---|
| JP | 2005-038892 A | 2/2005 |
| JP | 2006-165542 A | 6/2006 |

(Continued)

*Primary Examiner* — Jeffrey G Hoekstra
*Assistant Examiner* — Jason M Ip
(74) *Attorney, Agent, or Firm* — Oliff PLC

(57) ABSTRACT

A light emitting device includes a light emitting element that emits light, and a wiring substrate that includes a light reflective reflecting electrode to which the light emitting element is bonded using a bonding material. The reflecting electrode has a reflecting region which reflects light emitted from the light emitting element. An area of a mounting region surrounded by an outer circumference of the reflecting region is greater than an area of the light emitting element by four times or more seen in a direction perpendicular to the wiring substrate.

16 Claims, 5 Drawing Sheets

(56) References Cited

U.S. PATENT DOCUMENTS

2011/0245697 A1* 10/2011 Miettinen .......... A61B 5/02427
600/500
2016/0027973 A1* 1/2016 Maki .................... H01L 33/387
257/99
2016/0242659 A1 8/2016 Yamashita et al.

FOREIGN PATENT DOCUMENTS

| JP | 2007-329249 A | 12/2007 |
| --- | --- | --- |
| JP | 2008-016593 A | 1/2008 |
| JP | 2008-198962 A | 8/2008 |
| JP | 2008-258296 A | 10/2008 |
| JP | 2013-000378 A | 1/2013 |
| JP | 2013-254833 A | 12/2013 |
| JP | 2016-152840 A | 8/2016 |

* cited by examiner

LIGHT EMITTING DEVICE, BIOLOGICAL INFORMATION MEASURING APPARATUS, AND METHOD OF MANUFACTURING LIGHT EMITTING DEVICE

BACKGROUND

1. Technical Field

The present invention relates to a light emitting device which emits light.

2. Related Art

In the related art, a technology related to a light emitting device which emits light is proposed. For example, JP-A-2008-198962 discloses a light emitting device in which light emitted by a light emitting element bonded to a substrate is concentrated.

According to the technology in JP-A-2008-198962, light emitted by the light emitting element is concentrated using a reflective film formed on the substrate. However, according to the technology in JP-A-2008-198962, the reflective film is formed such that the light emitting element is bonded to a mounting portion on the substrate using a die bond material, and then the die bond material and the mounting portion are covered. Accordingly, a process of manufacturing a light emitting device is complicated.

SUMMARY

An advantage of some aspects of the invention is that a process of manufacturing a light emitting device is simplified.

A light emitting device includes a light emitting element that emits light, and a wiring substrate that includes a light reflective reflecting electrode to which the light emitting element is bonded using a bonding material. The reflecting electrode has a reflecting region which reflects light emitted from the light emitting element. An area of a mounting region surrounded by an outer circumference of the reflecting region is greater than an area of the light emitting element by four times or more seen in a direction perpendicular to the wiring substrate. In this configuration, the area of the mounting region surrounded by the outer circumference of the reflecting region reflecting light emitted from the light emitting element is greater than the area of the light emitting element by four times or more seen in the direction perpendicular to the wiring substrate. Therefore, even though a reflective film for reflecting light emitted from the light emitting element is not separately provided, the reflecting electrode can sufficiently reflect light emitted from the light emitting element. Thus, a process of manufacturing a light emitting device is simplified.

In a preferred example of the light emitting device according to the aspect of the invention, the area of the mounting region is greater than the area of the light emitting element by nine times or more seen in the direction perpendicular to the wiring substrate. In this configuration, the area of the mounting region is greater than the area of the light emitting element by nine times or more seen in the direction perpendicular to the wiring substrate. Therefore, compared to a configuration in which the area of the mounting region is smaller than the area of the light emitting element by nine times seen in the direction perpendicular to the wiring substrate, the reflecting electrode can further reflect light emitted from the light emitting element.

In a preferred example of the light emitting device according to the aspect of the invention, the area of the mounting region is greater than the area of the light emitting element by four hundred times or less seen in the direction perpendicular to the wiring substrate. In this configuration, the area of the mounting region is greater than the area of the light emitting element by four hundred times or less seen in the direction perpendicular to the wiring substrate. Therefore, it is possible to sufficiently ensure an area of the reflecting region without hindering miniaturization of the light emitting device.

In a preferred example of the light emitting device according to the aspect of the invention, the wiring substrate has a hole which is formed within a bonding region of the reflecting electrode where the light emitting element is bonded and into which the bonding material infiltrates. In this configuration, the wiring substrate has the hole which is formed within the bonding region where the light emitting element is bonded and into which the bonding material infiltrates. Therefore, compared to a configuration in which the wiring substrate has no hole which is formed within the bonding region and into which the bonding material infiltrates, the bonding material flowing out of the bonding region can be minimized. Thus, the area of the reflecting region can be prevented from being reduced.

In a preferred example of the light emitting device according to the aspect of the invention, the hole is formed entirely or partially along the reflecting electrode in a thickness direction. In this configuration, the hole into which the bonding material infiltrates is formed entirely or partially along the reflecting electrode in the thickness direction. Therefore, an influence of the bonding material on the wiring substrate can be minimized.

A biological information measuring apparatus according to an aspect of the invention includes the various light emitting devices described above. In this configuration, an operation and an effect similar to those of the various light emitting devices described above are achieved.

A method of manufacturing a light emitting device according to an aspect of the invention includes bonding a light emitting element which emits light and a light reflective reflecting electrode on a wiring substrate, using a bonding material. The reflecting electrode has a reflecting region which reflects light emitted from the light emitting element. An area of a mounting region surrounded by an outer circumference of the reflecting region is greater than an area of the light emitting element by four times or more seen in a direction perpendicular to the wiring substrate. In this method, a light emitting device, in which the light emitting element that emits light and the light reflective reflecting electrode on the wiring substrate are bonded to each other using the bonding material, the reflecting electrode has the reflecting region that reflects light emitted from the light emitting element, and the area of the mounting region surrounded by the outer circumference of the reflecting region is greater than the area of the light emitting element by four times or more seen in the direction perpendicular to the wiring substrate, is manufactured. Therefore, it is possible to manufacture a light emitting device in which the reflecting electrode sufficiently reflects light emitted from the light emitting element even though a reflective film for reflecting light emitted from the light emitting element is not separately provided. Thus, a process of manufacturing a light emitting device is simplified.

In a preferred example of the method of manufacturing a light emitting device according to the aspect of the invention, the wiring substrate has a hole which is formed within a bonding region where the light emitting element is bonded and into which the bonding material infiltrates. It is preferable that in bonding the light emitting element and the reflecting electrode, the light emitting element and the reflecting electrode are bonded to each other such that the bonding material flows into the hole. In this method, the light emitting element and the reflecting electrode are bonded to each other such that the bonding material flows into the hole which is formed within the bonding region where the light emitting element is bonded and into which the bonding material infiltrates. Therefore, the bonding material flowing out of the bonding region can be minimized. Thus, an area of the reflecting region can be prevented from being reduced.

BRIEF DESCRIPTION OF THE DRAWINGS

The invention will be described with reference to the accompanying drawings, wherein like numbers reference like elements.

DESCRIPTION OF EXEMPLARY EMBODIMENTS

First Embodiment

A biological information measuring apparatus 100 of a first embodiment is a measuring instrument for measuring biological information of a test subject and is mounted on a site (hereinafter, will be referred to as the "measurement site") M that is a measurement target in the body of the test subject. For example, the measurement site M is a wrist or an ankle. In the first embodiment, a pulse rate of the test subject is illustrated as the biological information.

Figure 1:
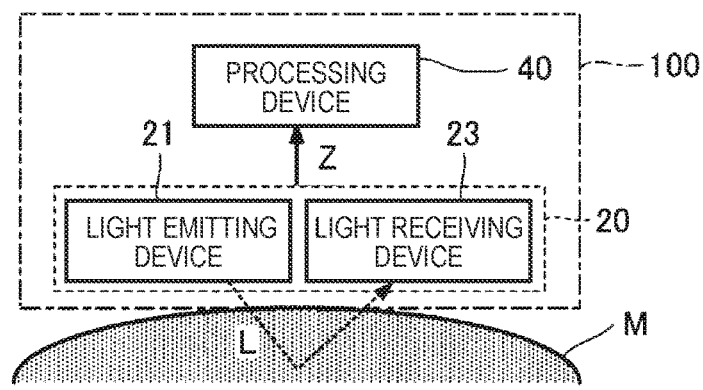
FIG. 1 is a view of a configuration of a measuring apparatus according to a first embodiment of the invention.

FIG. 1 is a view of a configuration focused on a function of the biological information measuring apparatus 100. As illustrated in FIG. 1, the biological information measuring apparatus 100 of the first embodiment includes a detecting device 20 and a processing device 40. The detecting device 20 is a sensor module generating a detection signal Z in accordance with the state of the measurement site M. The detecting device 20 of the first embodiment generates the detection signal Z to be used for specifying the pulse rate of the test subject. As illustrated in FIG. 1, the detecting device 20 includes a light emitting device 21 and a light receiving device 23. The light emitting device 21 and the light receiving device 23 are installed on a surface of the biological information measuring apparatus 100 facing the measurement site M (hereinafter, will be referred to as the "detection surface"). The detection surface is a flat surface or a curved surface. The light emitting device 21 emits light L to the measurement site M. The light receiving device 23 generates the detection signal Z corresponding to the light reception level of the light L arrived from the measurement site M. The light emitting device 21 and the light receiving device 23 may be integrated in one device or may be separate devices.

Figure 2:
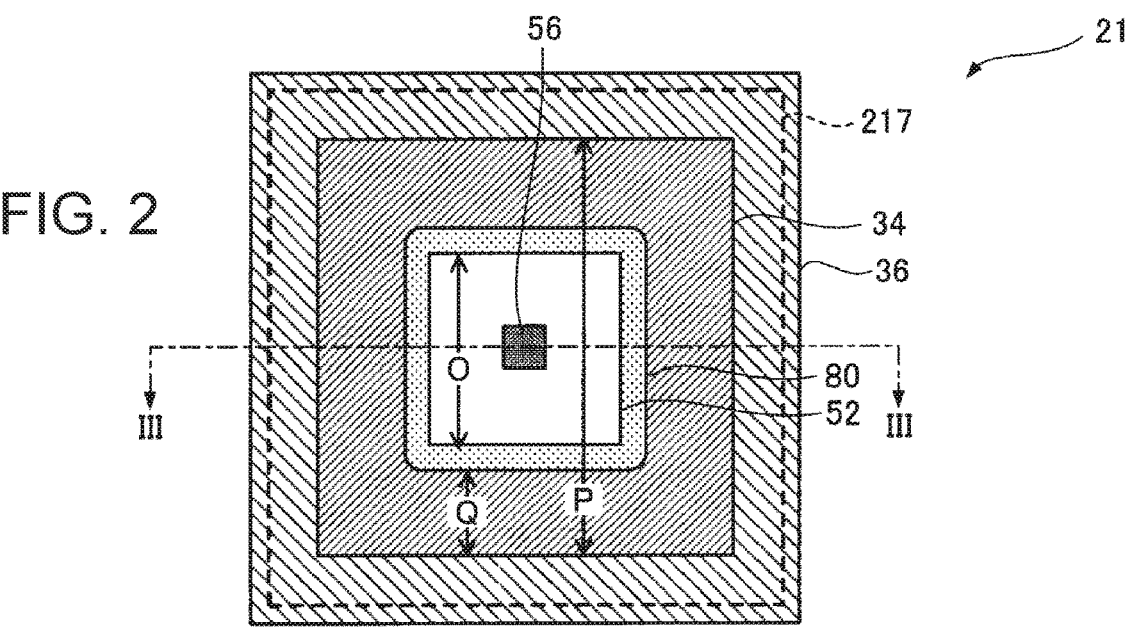
FIG. 2 is a plan view of a light emitting device.
Figure 3:
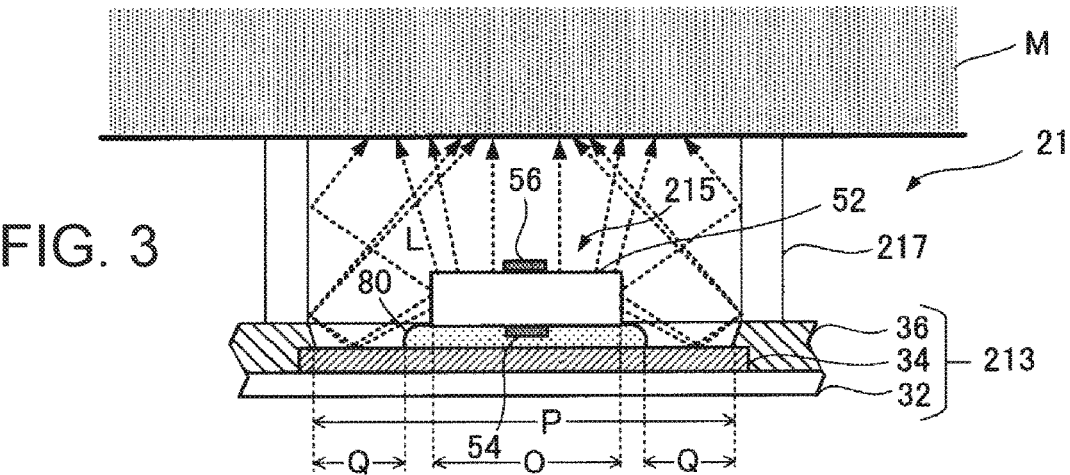
FIG. 3 is a cross-sectional view of the light emitting device.

FIG. 2 a plan view of the light emitting device 21, and FIG. 3 is a cross-sectional view taken along line III-III in FIG. 2. The light emitting device 21 includes a wiring substrate 213, a light emitting element 215, and a partition wall 217. The light emitting element 215 is mounted on the front surface of the wiring substrate 213. The wiring substrate 213 and the light emitting element 215 are electrically connected to each other. As illustrated in FIG. 3, the wiring substrate 213 includes a base material 32, a reflecting electrode 34, and a resist 36.

For example, the base material 32 is a rigid substrate (a single layer substrate or a multi-layer substrate) formed of glass epoxy. The light reflective reflecting electrode 34 and an electronic circuit (not illustrated) supplying power to the light emitting element 215 via the reflecting electrode 34 are mounted on the front surface of the base material 32. The reflecting electrode 34 is a thin-film electrode formed of metal (for example, gold or silver) having high light reflectivity. The front surface of the base material 32 is covered with the resist 36. The resist 36 is a protective film for protecting the base material 32. As illustrated in FIGS. 2 and 3, a part overlapping the reflecting electrode 34 is selectively removed. That is, the reflecting electrode 34 is exposed from the resist 36. Hereinafter, a region in the reflecting electrode 34 exposed from the resist 36 will be referred to as the "mounting region P". The light emitting element 215 is mounted on the front surface of the mounting region P. In the first embodiment, the area of the mounting region P is greater than the area of the light emitting element 215 by four times seen in a direction perpendicular to the wiring substrate 213. For example, the mounting region P has a substantially square shape.

As illustrated in FIG. 3, the light emitting element 215 has a light emitting unit 52, a first electrode 54, and a second electrode 56. The light emitting unit 52 emits the light L to the measurement site M. For example, a light emitting diode (LED) which emits incoherent light L is preferably utilized as the light emitting unit 52. The light emitting unit 52 of the first embodiment radially emits the light L. That is, the light L from the light emitting unit 52 travels not only to the measurement site M side but also to a side opposite to the measurement site M. For example, the light emitting unit 52 has a cubic shape including a substantially square surface on which the first electrode 54 is positioned and a substantially square surface on which the second electrode 56 is positioned. The first electrode 54 (for example, anode) is positioned on a surface of the light emitting unit 52 bonded to the base material 32. The second electrode 56 (for example, cathode) is installed on a surface of the light emitting unit 52 opposite to the surface on which the first electrode 54 is positioned. When power supplied from the base material 32 to the first electrode 54 flows to the second electrode 56, the light emitting unit 52 emits the light L.

The light emitting element 215 and the reflecting electrode 34 are bonded to each other using a bonding material 80. Specifically, as illustrated in FIG. 2, the surface of the light emitting element 215 on which the first electrode 54 is disposed and the front surface of the reflecting electrode 34 are bonded to each other using the bonding material 80 such that the center of the mounting region P and the center of the light emitting unit 52 coincide with each other in a planar view. For example, the bonding material 80 is a paste which contains conductive metal (for example, silver or gold) having high light reflectivity. The bonding material 80 has low reflectivity compared to the reflecting electrode 34. When the light emitting element 215 and the reflecting electrode 34 are bonded to each other using the bonding material 80, the first electrode 54 becomes conductive with respect to the reflecting electrode 34. Hereinafter, a region of the reflecting electrode 34 where the light emitting element 215 is bonded will be referred to as the "bonding region O". As illustrated in FIG. 3, the bonding region O is a region surrounded by the outer circumference of the light emitting element 215 in the mounting region P when seen in the direction perpendicular to the wiring substrate 213 and has a substantially square shape. In the first embodiment, the bonding material 80 is interposed between the reflecting electrode 34 and the first electrode 54. However, it is also possible to employ a configuration in which the light emitting element 215 and the reflecting electrode 34 are bonded to each other using the bonding material 80 such that the reflecting electrode 34 and the first electrode 54 are in contact with each other. The bonding material 80 is pressed when the light emitting element 215 and the reflecting electrode 34 are bonded to each other, thereby flowing out of the bonding region O on the front surface of the reflecting electrode 34. Therefore, as illustrated in FIG. 2, the outer circumference of the bonding material 80 can be closer to the outer circumference of the mounting region P than the bonding region O. The first embodiment illustrates a configuration in which the outer circumference of the bonding material 80 is closer to the outer circumference of the mounting region P than the bonding region O.

The reflecting electrode 34 has a reflecting region Q which reflects the light L emitted from the light emitting element 215. As illustrated in FIG. 2, the reflecting region Q is a region exposed from the light emitting element 215 and the bonding material 80 in the mounting region P. The reflecting region Q of the first embodiment is a rectangular frame-shaped region realized by removing the region surrounded by the outer circumference of the bonding material 80 from the region surrounded by the outer circumference of the mounting region P in FIG. 2 when seen in the direction perpendicular to the front surface of the wiring substrate 213 on which the light emitting element 215 is mounted. The area of the mounting region P increases when the area of the reflecting region Q is increased. The mounting region P can also be referred to as a region surrounded by the outer circumference of the reflecting region Q.

The partition wall 217 in FIG. 3 is installed on the front surface of the resist 36 so as to surround the light emitting element 215 and reflects the light L emitted from the light emitting element 215. For example, the partition wall 217 is formed of metal or a resin material having light reflective properties. The light L radially emitted from the light emitting element 215 reaches the measurement site M directly from the light emitting element 215 or indirectly after being reflected by an inner wall surface of the partition wall 217 and the reflecting region Q. The light L which has arrived at the measurement site M is repetitively reflected and scattered underneath the measurement site M and is then emitted to the detection surface side, thereby arriving at the light receiving device 23. That is, the light emitting device 21 and the light receiving device 23 function as a reflective optical sensor.

The light receiving device 23 generates the detection signal Z corresponding to the light reception level of the light L arrived from the measurement site M. For example, a photoelectric conversion element such as a photo diode (PD) which receives the light L with a light receiving surface facing the measurement site M is preferably utilized as the light receiving device 23. For example, the detecting device 20 includes a drive circuit which drives the light emitting unit 52 when a driving current is supplied, and output circuits (for example, an amplifier circuit and an A/D converter) which perform amplification and A/D conversion of an output signal from the light receiving device 23. The circuits are not illustrated in FIG. 1.

A blood vessel underneath the measurement site M expands and contracts repetitively in the same cycle as the pulsation. Since a blood flow rate inside a blood vessel varies between an expansion phase and a contraction phase, the detection signal Z generated by each light receiving device 23 in accordance with the light reception level from the measurement site M is a pulse wave signal including a cyclic fluctuation component corresponding to the fluctuation of the blood flow rate in a blood vessel underneath the measurement site M.

The processing device 40 in FIG. 1 specifies a pulse rate of the test subject based on the detection signal Z generated by the detecting device 20. A known technology can be arbitrarily employed for specifying a pulse rate. For example, the processing device 40 provides the test subject with the specified pulse rate through a display.

Here, when the quantity of the light L which is emitted from the light emitting element 215 and arrives at the measurement site M increases, it is possible to generate the detection signal Z which properly indicates the state inside the measurement site M. Thus, the biological information can be specified with higher accuracy. The reflecting electrode 34 of the first embodiment functions as a reflective film for reflecting the light L emitted from the light emitting element 215, in addition to the function as an electrode, by setting the area of the mounting region P to be greater than the area of the light emitting element 215 by four times seen in the direction perpendicular to the wiring substrate 213. As a configuration for increasing the quantity of the light L arriving at the measurement site M, in addition to the configuration of the first embodiment utilizing the reflecting electrode 34 as a reflective film, for example, it is also possible to employ a configuration in which a reflective film is separately provided such that the light emitting element 215 of the wiring substrate 213 is surrounded. However, according to the configuration of the first embodiment in which the area of the mounting region P is set to be greater than the area of the light emitting element 215 by four times seen in the direction perpendicular to the wiring substrate 213, even though a reflective film for reflecting the light L emitted from the light emitting element 215 is not separately provided, the reflecting electrode 34 can sufficiently reflect the light L emitted from the light emitting element 215. Thus, the process of manufacturing the light emitting device 21 is simplified.

Second Embodiment

Figure 4:
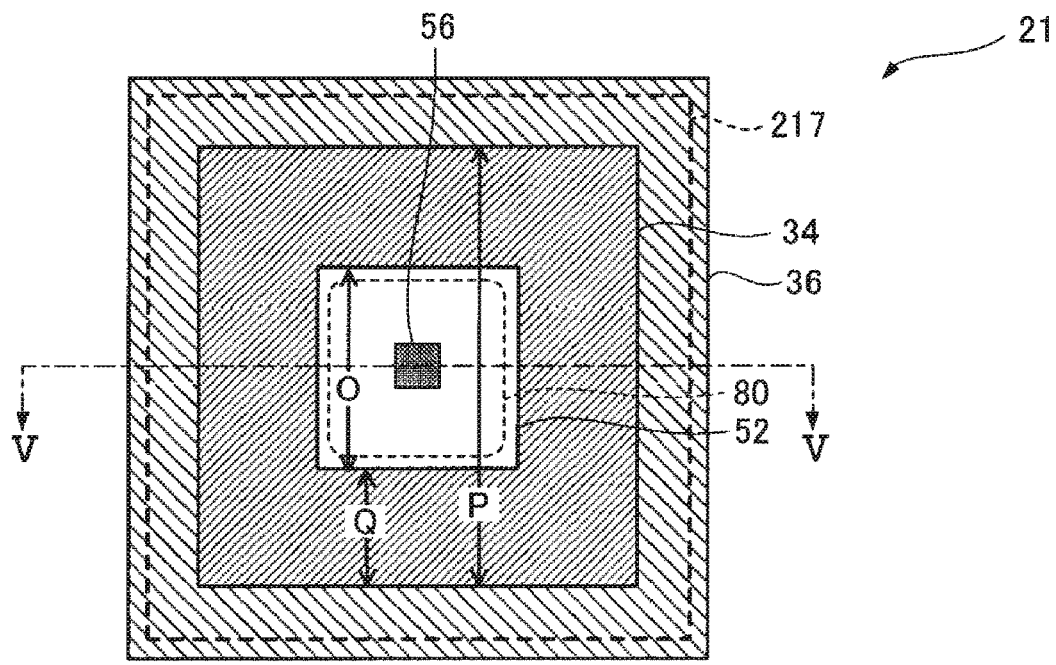
FIG. 4 is a plan view of a light emitting device according to a second embodiment.
Figure 5:
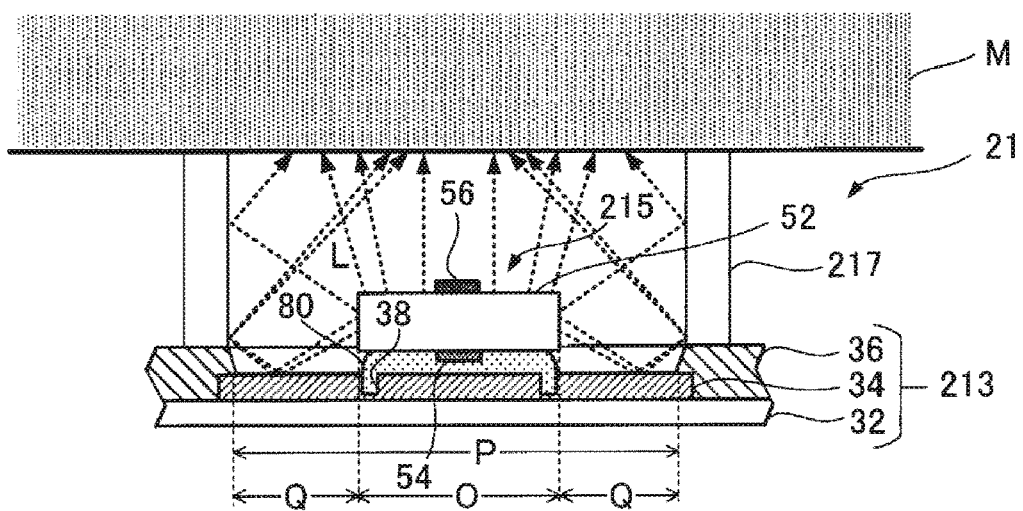
FIG. 5 is a cross-sectional view of the light emitting device.

FIG. 4 is a plan view of a light emitting device 21 according to the second embodiment, and FIG. 5 is a cross-sectional view taken along line V-V in FIG. 4. As illustrated in FIG. 5, similar to the first embodiment, the light emitting device 21 of the second embodiment includes the wiring substrate 213, the light emitting element 215, and the partition wall 217. However, the wiring substrate 213 of the second embodiment has holes 38 in which the bonding material 80 infiltrates.

Figure 6:
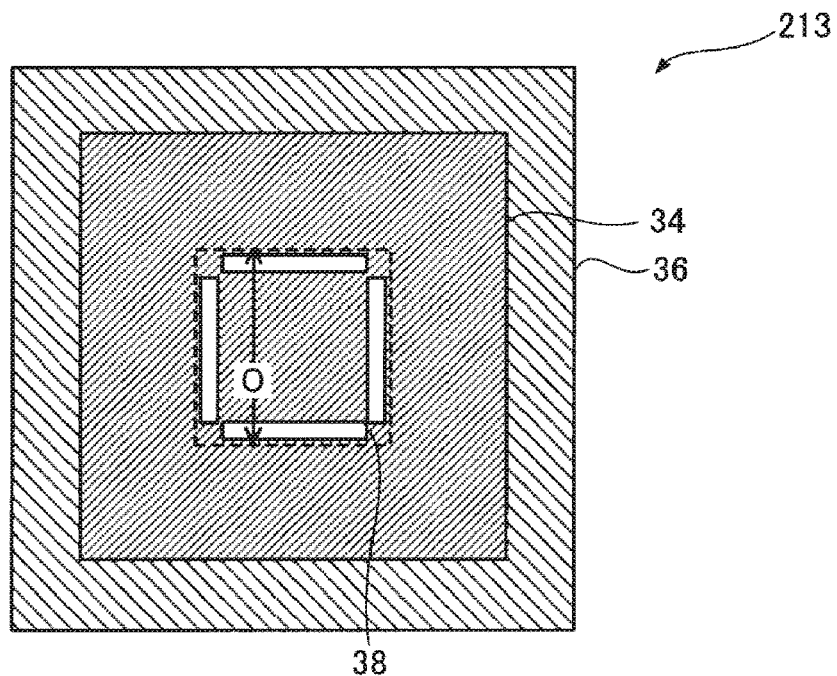
FIG. 6 is a plan view of a base material before a light emitting element is bonded.

FIG. 6 is a plan view of the base material 32 before the light emitting element 215 is bonded. As illustrated in FIG. 6, the holes 38 are formed within the bonding region O. In the second embodiment, four holes 38 are formed within the bonding region O. Specifically, the holes 38 form a rectangular shape having each thereof along a side the outer circumference of the bonding region O. In order to maintain the reflecting electrode 34 and the light emitting element 215 being electrically connected to each other, no hole 38 is formed on the four corners of the bonding region O. As illustrated in FIG. 5, the holes 38 of the second embodiment are closed-end holes (groove portions) formed partially along the reflecting electrode 34 in the thickness direction. Similar to the first embodiment, the light emitting element 215 is bonded to the reflecting electrode 34 using the bonding material 80. In the second embodiment, as illustrated in FIG. 5, the light emitting element 215 and the reflecting electrode 34 are bonded to each other such that the bonding material 80 flows into the holes 38 formed within the bonding region O.

In the first embodiment, the bonding material 80 is pressed when the light emitting element 215 and the reflecting electrode 34 are bonded to each other, thereby flowing out of the bonding region O as illustrated in FIGS. 2 and 3. However, as described above, the bonding material 80 has reflectivity lower than that of the reflecting electrode 34. Therefore, ideally, it is desired that the bonding material 80 does not flow out of the bonding region O. In the second embodiment, since the bonding material 80 is pressed when the light emitting element 215 and the reflecting electrode 34 are bonded to each other, and flows into the holes 38 formed in the reflecting region Q as illustrated in FIG. 5, the bonding material 80 does not flow out of the bonding region O. Therefore, as illustrated in FIG. 6, the reflecting region Q of the second embodiment is a rectangular frame-shaped region realized by removing the region surrounded by the outer circumference of the light emitting element 215 from the region surrounded by the outer circumference of the mounting region P when seen in the direction perpendicular to the wiring substrate 213.

As illustrated in FIG. 5, similar to the first embodiment, the light L radially emitted from the light emitting element 215 of the light emitting device 21 reaches the measurement site M directly from the light emitting element 215 or indirectly after being reflected by the partition wall 217 and the reflecting region Q. The light L which has arrived at the measurement site M is repetitively reflected and scattered underneath the measurement site M and is then emitted to the detection surface side, thereby arriving at the light receiving device 23. The light receiving device 23 generates the detection signal Z corresponding to the light reception level of the light L arriving from the measurement site M. Similar to the first embodiment, the processing device 40 in FIG. 1 specifies a pulse rate based on the detection signal Z generated by the detecting device 20 and provides the test subject with the specified pulse rate.

An effect similar to that of the first embodiment is also realized in the second embodiment. Particularly in the second embodiment, since the holes 38 into which the bonding material 80 flows are included within the bonding region O, the bonding material 80 flowing out of the bonding region O can be minimized. Therefore, the area of the reflecting region Q can be prevented from being reduced. Thus, it is possible to further increase the quantity of the light L which is emitted from the light emitting element 215 and arrives at the measurement site M.

Modification Examples

Each of the embodiments illustrated above can be variously deformed. Forms of specific deformation will be illustrated below. It is also possible to appropriately combine two or more forms which are arbitrarily selected from the examples below.

(1) In each of the embodiments described above, the area of the mounting region P is greater than the area of the light emitting element 215 by four times seen in the direction perpendicular to the wiring substrate 213. However, the area of the mounting region P is arbitrary as long as the area of the mounting region P is greater than the area of the light emitting element 215 by four times or more seen in the direction perpendicular to the wiring substrate 213. For example, it is possible to preferably employ a configuration in which the area of the mounting region P is greater than the area of the light emitting element 215 by nine times or more seen in the direction perpendicular to the wiring substrate 213. However, from the viewpoint of miniaturizing the light emitting device 21, it is desirable to have a configuration in which the area of the mounting region P is greater than the area of the light emitting element 215 by four hundred times or less seen in the direction perpendicular to the wiring substrate 213.

(2) In each of the embodiments described above, the light emitting unit 52 has a cubic shape including the substantially square surface on which the first electrode 54 is positioned and the substantially square surface on which the second electrode 56 is positioned. However, the shape of the light emitting unit 52 is arbitrary. For example, it is also possible to employ a configuration in which the light emitting unit 52 has a columnar shape including a circular surface on which the first electrode 54 is positioned and a circular surface on which the second electrode 56 is positioned.

(3) In each of the embodiments described above, the mounting region P has a substantially square shape. However, the shape of the mounting region P is arbitrary. For example, it is also possible to employ a configuration in which the mounting region P has a circular shape.

(4) In each of the embodiments described above, the reflecting electrode 34 and the light emitting device 21 are bonded to each other such that the center of the mounting region P and the center of the light emitting unit 52 coincide with each other in a planar view. However, the bonding form of the reflecting electrode 34 and the light emitting device 21 is arbitrary as long as the light emitting unit 52 is positioned within the mounting region P in a planar view. However, according to the configuration in which the reflecting electrode 34 and the light emitting device 21 are bonded to each other such that the center of the mounting region P and the center of the light emitting unit 52 coincide with each other in a planar view, it is possible for the reflecting electrode 34 to further reflect light emitted from the light emitting element 215.

Figure 7:
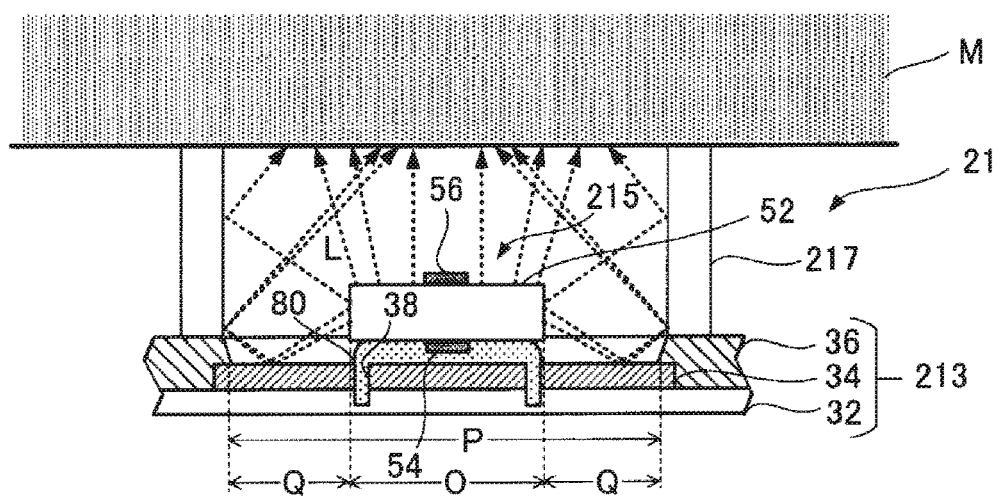
FIG. 7 is a cross-sectional view of a light emitting device according to Modification Example.

(5) The second embodiment illustrates a configuration including the holes 38 which are formed partially along the reflecting electrode 34 in the thickness direction and into which the bonding material 80 infiltrates (that is, a configuration in which the bottoms of the holes 38 are positioned in the reflecting electrode). However, it is also possible to employ a configuration in which the holes 38 are formed entirely along the reflecting electrode 34 in the thickness direction (that is, a configuration in which the reflecting electrode 34 is penetrated). As in the holes 38 illustrated in FIG. 7, it is also possible to employ a configuration in which the holes 38 penetrate the reflecting electrode 34 and are formed partially along the base material 32 in the thickness direction (that is, a configuration in which the bottoms of the holes 38 are positioned in the base material 32). As understood from the description above, the depth of the hole 38 is arbitrary as long as the holes 38 are formed within the bonding region O on the reflecting electrode 34. However, the configuration in which the holes 38 are formed entirely or partially along the reflecting electrode 34 in the thickness direction has an advantage in that an influence of the bonding material 80 on the base material 32 can be minimized compared to a configuration in which the bottoms of the holes 38 are positioned in the base material 32. Meanwhile, the configuration in which the bottoms of the holes 38 are positioned in the base material 32 has large volume of space for an extra bonding material 80 to flow therein, compared to a configuration in which the hole 38 is formed entirely or partially along the reflecting electrode 34 in the thickness direction. Therefore, the bonding material 80 flowing out of the bonding region O can be minimized.

Figure 8:
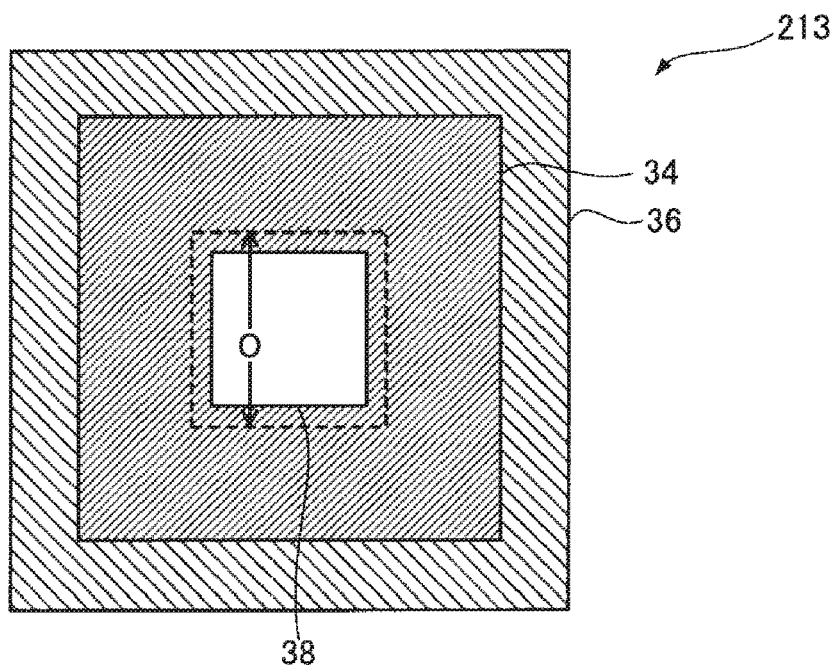
FIG. 8 is a plan view of a light emitting device according to another Modification Example.
Figure 9:
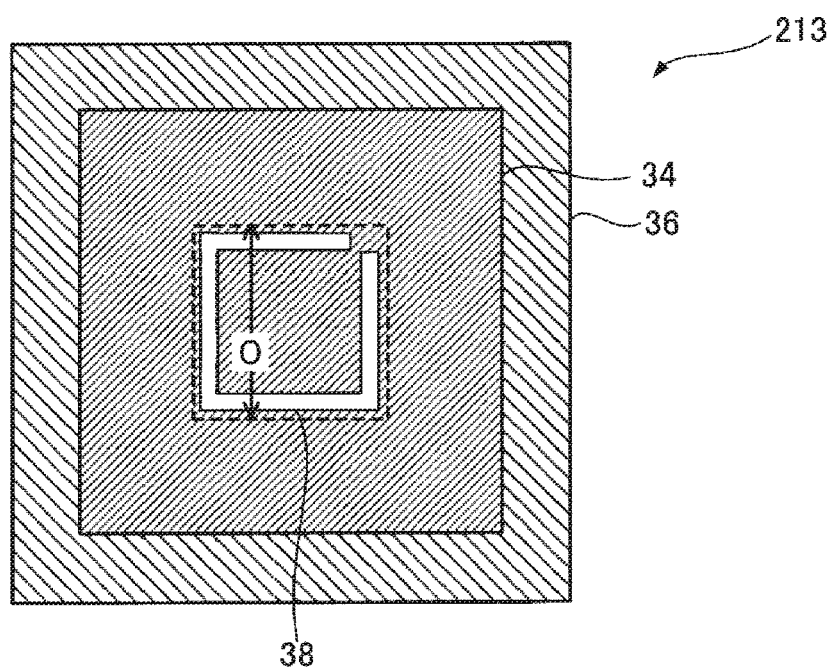
FIG. 9 is a plan view of a light emitting device according to further another Modification Example.

(6) The second embodiment illustrates a configuration in which four rectangular-shaped holes 38 are formed within the bonding region O. However, the number and the shape of the holes 38 are not limited to the illustrated example. For example, it is also possible to employ a configuration in which one hole 38 is formed in a region smaller than the bonding region O (FIG. 8), or a configuration in which one hole 38 is formed along all of the sides except for one corner of the bonding region O (FIG. 9). The number and the shape of the holes 38 are arbitrary as long as electrical connection between the light emitting element 215 and the reflecting electrode 34 is ensured.

Figure 10:
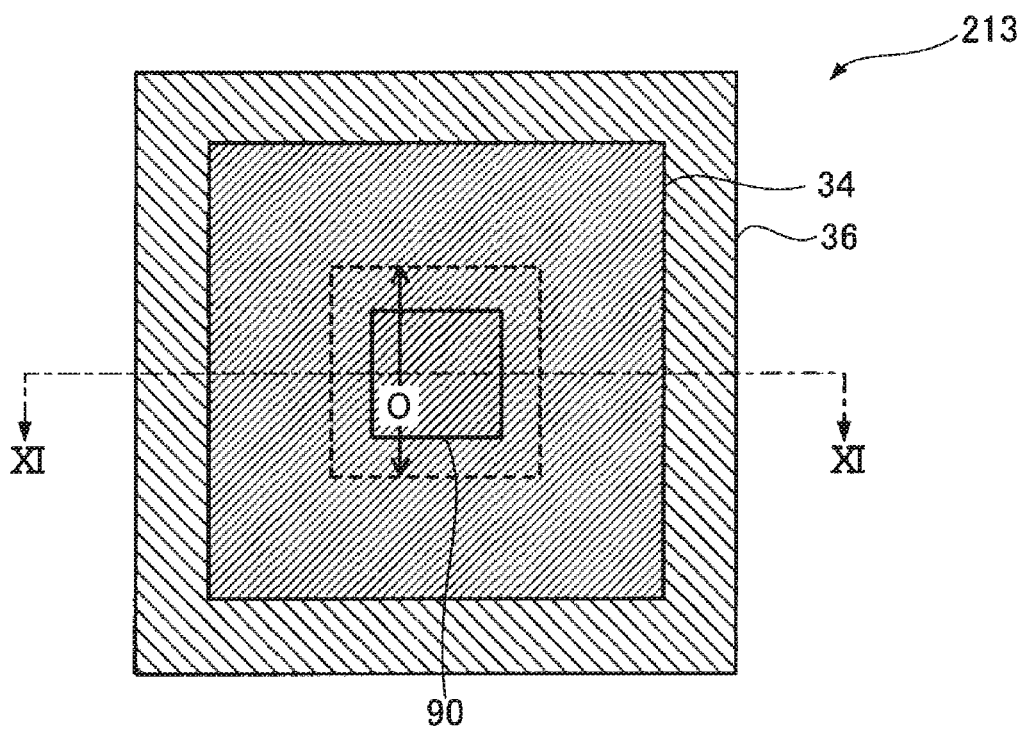
FIG. 10 is a plan view of a light emitting device according to still another Modification Example.
Figure 11:
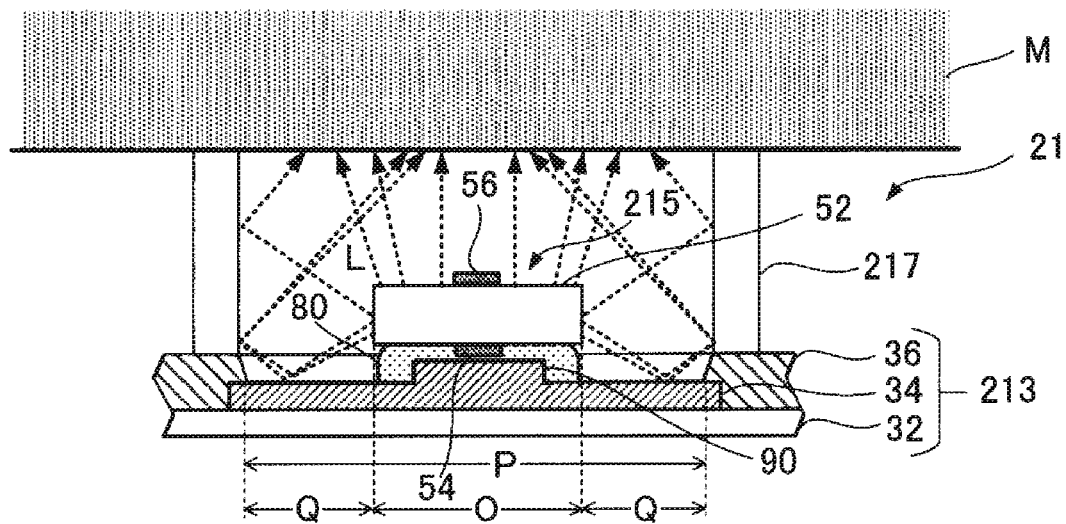
FIG. 11 is a cross-sectional view of the light emitting device according to still another Modification Example.

In addition, as illustrated in FIG. 10, it is also possible to employ a configuration in which a projection portion 90 is integrally provided with the reflecting electrode 34 within the bonding region O. According to the configuration above, as illustrated in FIG. 11, the bonding material 80 stays in the peripheral space of the projection portion 90. Therefore, it is possible to realize an effect similar to that of the second embodiment in that the bonding material 80 flowing out of the bonding region O is minimized.

(7) In each of the embodiments described above, the LED which emits incoherent light L is illustrated as the light emitting unit 52. However, it is also possible to utilize a vertical cavity surface emitting laser (VCSEL), a photonic crystal laser, or the like which emits coherent light (that is, laser light) as the light emitting unit 52. However, each of the embodiments described above in which the reflecting electrode 34 also functions as a reflective film is particularly effective for a case where the LED radially emits the light L.

The entire disclosure of Japanese Patent Application No. 2017-001672 is hereby incorporated herein by reference.

What is claimed is:

1. A light emitting device comprising:
   a light emitting element; and
   a wiring substrate that includes a substrate, a light reflecting electrode formed on the substrate and to which the light emitting element is bonded using a bonding material, and a resist that covers the substrate and the reflecting electrode and has an opening that exposes the light reflecting electrode in a portion that overlaps the light reflecting electrode in a plan view, wherein
   the light reflecting electrode has a reflecting region which reflects light emitted from the light emitting element,
   the light emitting element has a light emitter, a first electrode and a second electrode,
   an area of a mounting region surrounded by an outer circumference of the reflecting region is greater than an area of the light emitting element by four times or more seen in a direction perpendicular to the wiring substrate, and
   an inner peripheral edge of the opening in the resist is located inside an outer peripheral edge of the reflective electrode in the plan view.

2. The light emitting device according to claim 1, wherein the area of the mounting region is greater than the area of the light emitting element by nine times or more seen in the direction perpendicular to the wiring substrate.

3. The light emitting device according to claim 1, wherein the area of the mounting region is greater than the area of the light emitting element by four hundred times or less seen in the direction perpendicular to the wiring substrate.

4. The light emitting device according to claim 1, wherein the wiring substrate has a hole which is formed within a bonding region of the light reflecting electrode where the light emitting element is bonded and into which the bonding material infiltrates.

5. The light emitting device according to claim 4, wherein the hole is formed entirely or partially along the light reflecting electrode in a thickness direction.

6. A biological information measuring apparatus comprising:
   the light emitting device according to claim 1,
   wherein the biological information measuring apparatus measures biological information of a test subject.

7. A biological information measuring apparatus comprising:
   the light emitting device according to claim 2,
   wherein the biological information measuring apparatus measures biological information of a test subject.

8. A biological information measuring apparatus comprising:
   the light emitting device according to claim 3,
   wherein the biological information measuring apparatus measures biological information of a test subject.

9. A biological information measuring apparatus comprising:
   the light emitting device according to claim 4,
   wherein the biological information measuring apparatus measures biological information of a test subject.

10. A biological information measuring apparatus comprising:
    the light emitting device according to claim 5,
    wherein the biological information measuring apparatus measures biological information of a test subject.

11. The light emitting device according to claim 1, wherein a reflective film is not provided on the wiring substrate between the reflecting electrode and the light emitting element.

12. The light emitting device according to claim 1, wherein the wiring substrate comprises a base material, and the first electrode is on a first surface of the light emitter and the first surface of the light emitter is bonded to the base material.

13. The light emitting device according to claim 12, wherein the second electrode is on a second surface of the light emitter opposite the first surface.

14. The light emitting device according to claim 1, further comprising
a partition wall formed of a material having light reflective properties.

15. A method of manufacturing a light emitting device comprising:
bonding a light emitting element and a light reflecting electrode on a wiring substrate, using a bonding material, and
covering the wiring substrate and to the light reflecting electrode with a resist while leaving an opening that exposes to the light reflecting electrode in a portion that overlaps to the light reflecting electrode in a plan view, wherein
to the light reflecting electrode has a reflecting region which reflects light emitted from the light emitting element,
the light emitting element has a light emitter, a first electrode and a second electrode,
an area of a mounting region surrounded by an outer circumference of the reflecting region is greater than an area of the light emitting element by four times or more seen in a direction perpendicular to the wiring substrate, and
an inner peripheral edge of the opening in the resist is located inside an outer peripheral edge of the light reflecting electrode in the plan view.

16. The method of manufacturing a light emitting device according to claim 15,
wherein the wiring substrate has a hole which is formed within a bonding region where the light emitting element is bonded and into which the bonding material infiltrates, and
wherein in the bonding of the light emitting element and the light reflecting electrode, the light emitting element and the light reflecting electrode are bonded to each other such that the bonding material flows into the hole.

* * * * *